US006767936B2

(12) United States Patent
Walz et al.

(10) Patent No.: US 6,767,936 B2
(45) Date of Patent: Jul. 27, 2004

(54) DENTAL COMPOSITIONS COMPRISING BISACRYLAMIDES AND USE THEREOF

(75) Inventors: Uwe Walz, Constance (DE); Joachim E. Klee, Radolfzell (DE)

(73) Assignee: Dentsply DeTrey GmbH (DE)

(*) Notice: Subject to any disclaimer, the term of this patent is extended or adjusted under 35 U.S.C. 154(b) by 0 days.

(21) Appl. No.: 10/308,564

(22) Filed: Dec. 3, 2002

(65) Prior Publication Data

US 2003/0130373 A1 Jul. 10, 2003

Related U.S. Application Data

(62) Division of application No. 09/925,173, filed on Aug. 9, 2001, now abandoned.
(60) Provisional application No. 60/224,670, filed on Aug. 11, 2000, and provisional application No. 60/310,572, filed on Aug. 7, 2001.

(51) Int. Cl.$^7$ .............................. A61K 6/10; C08F 2/46

(52) U.S. Cl. ..................... 523/105; 523/109; 523/113; 523/115; 523/116; 523/118; 522/47; 524/323

(58) Field of Search ........................ 523/105, 109, 523/113, 115, 116, 118; 522/47; 524/323

(56) References Cited

U.S. PATENT DOCUMENTS

| | | | | |
|---|---|---|---|---|
| 3,787,213 A | * | 1/1974 | Gervay et al. | 430/292 |
| 3,997,504 A | * | 12/1976 | Plymale | 523/116 |
| 4,089,763 A | | 5/1978 | Dart et al. | 204/159.23 |
| 4,297,266 A | | 10/1981 | Ibsen et al. | 260/42.14 |
| 4,323,348 A | | 4/1982 | Schmitz-Josten et al. | 433/228 |
| 4,386,912 A | | 6/1983 | Nagase et al. | 433/228 |
| 4,457,818 A | | 7/1984 | Denyer et al. | 204/159.19 |
| 4,525,256 A | | 6/1985 | Martin | 204/159.18 |
| 4,558,120 A | | 12/1985 | Tomalia et al. | 528/363 |
| 4,587,329 A | | 5/1986 | Tomalia et al. | 528/363 |
| 4,674,980 A | | 6/1987 | Ibsen et al. | 433/228.1 |
| 4,746,686 A | | 5/1988 | Waller | 522/14 |
| 4,857,599 A | | 8/1989 | Tomalia et al. | 525/259 |
| 4,952,241 A | | 8/1990 | Reiners et al. | 106/35 |
| 5,274,064 A | | 12/1993 | Sarkar | 528/25 |
| 5,308,886 A | | 5/1994 | Masuhara et al. | 522/81 |
| 5,395,883 A | | 3/1995 | Yates, III et al. | 525/89 |
| 5,418,301 A | | 5/1995 | Hult et al. | 525/437 |
| 5,468,789 A | | 11/1995 | Lewis et al. | 524/99 |
| 5,486,548 A | | 1/1996 | Podszun et al. | 523/115 |
| 5,530,092 A | | 6/1996 | Meijer et al. | 528/363 |
| 5,545,676 A | | 8/1996 | Palazzotto et al. | 522/15 |
| 5,624,976 A | | 4/1997 | Klee | 523/116 |
| 5,679,794 A | | 10/1997 | Suhadolnik et al. | 546/186 |
| 5,709,548 A | * | 1/1998 | Oxman et al. | 433/218 |
| 5,767,170 A | | 6/1998 | Ibsen et al. | 522/81 |
| 5,814,681 A | | 9/1998 | Hino et al. | 523/113 |
| 5,834,118 A | | 11/1998 | Ranby et al. | 428/482 |
| 5,847,020 A | | 12/1998 | Ibsen et al. | 522/84 |
| 5,847,025 A | | 12/1998 | Moszner et al. | 523/116 |
| 5,886,064 A | | 3/1999 | Rheinberger et al. | 523/116 |
| 5,914,379 A | | 6/1999 | Sutoris et al. | 526/204 |
| 5,969,000 A | | 10/1999 | Yang et al. | 523/116 |
| 5,985,958 A | | 11/1999 | Moszner et al. | 524/83 |
| 6,025,114 A | | 2/2000 | Popat et al. | 430/284.1 |
| 6,030,606 A | | 2/2000 | Holmes | 424/49 |
| 6,031,016 A | | 2/2000 | Ibsen et al. | 522/79 |
| 6,121,344 A | | 9/2000 | Angeletakis et al. | 523/116 |
| 6,136,885 A | | 10/2000 | Rusin et al. | 523/116 |
| 6,184,339 B1 | | 2/2001 | Stansbury et al. | 528/407 |

FOREIGN PATENT DOCUMENTS

| | | |
|---|---|---|
| DE | 22 11 128 | 9/1973 |
| DE | 3 703 080 | 1/1988 |
| DE | 3 703 120 | 1/1988 |
| DE | 295 645 | 7/1990 |
| EP | 023 686 | 7/1980 |
| EP | 049 599 | 9/1981 |
| EP | 059 649 | 3/1982 |
| EP | 102 199 | 8/1983 |
| EP | 140 140 | 9/1984 |
| EP | 254 950 | 7/1987 |
| EP | 630 640 | 12/1994 |
| EP | 673 637 | 9/1995 |
| EP | 765 856 | 9/1995 |
| EP | 716 103 | 11/1995 |
| EP | 995 421 | 10/1999 |
| SU | 334 845 | 1/1984 |
| WO | 92/21314 | 12/1992 |
| WO | 93/10176 | 5/1993 |
| WO | 93/12759 | 7/1993 |
| WO | 96/07688 | 3/1996 |
| WO | 97/02328 | 1/1997 |
| WO | 97/47272 | 12/1997 |

OTHER PUBLICATIONS

Standish et al; "Cure of Resin Based Restorative Materials; I. Self Cure Resins"; Australian Dental Journal; Apr. 1983; vol. 28; No. 2; pp. 82–86.

Cook et al; "Cure of Resin Based Restorative Materials; II. White Light Photopolymerizable Resins"; Australian Dental Journal; Oct. 1983; vol. 28; No. 5;. pp. 307–311.

Standish et al; "Polymerization Kinetics of Resin–Based Restorative Materials"; Journal of Biomedical Materials Research; vol. 17, pp. 275–282 (1983).

Liso et al; "Analysis of the Leaching and Toxicity of New Amine Activators for the Curing of Acrylic Bone Cements and Composites"; Biomaterials 18 (1997) pp. 15–20; 1996 Elsevier Science Limited.

(List continued on next page.)

*Primary Examiner*—Tae H. Yoon
(74) *Attorney, Agent, or Firm*—Douglas J. Hura; James B. Bieber

(57) ABSTRACT

The invention concerns a dental composition comprising bisacrylamides that are polymerizable by free-radical polymerization and by Michael-addition polymerization with amines. The application of polymerization and addition polymerization with amines opens the possibility to completely reacted materials that have no oxygen inhibited layers. The claimed bisacrylamides have an improved hydrolytic stability.

1 Claim, No Drawings

OTHER PUBLICATIONS

Kannurpatti et al; "Polymerization Behavior and Properties of Networks Formed by Dimethacrylate Dental Resins"; Division of Polymer Chemistry, Inc.; American Chemical Society; vol. 38; No. 2; Sep. 1997; pp. 106–107.

Cook et al; "A Simple Method for the Measurement of Polumerixation Shrinkage Dental Composites" Dental Materials 15 (1999); pp. 447–449.

NCBI National Liberty of Medicine; Br J Nutr 1998 Aug; 80 Suppl 1; S77–112; "Functional Food Science and Defence Against Reactive Oxidative Species"; 2 pgs.

NCBI National Library of Medicine; Crit Rev Food Sci Nutr 1994; 34(5–6): 47–97; "Antioxidants and Hormone–Mediated Health Benefits of Whole Grains"; 1 page.

NCBI National Liberty of Medicine; Santorro; Effect of Filler Content on the Profile of Released Biodegradation Products in Micro–Filled bis–GMA/TEGDMA Dental Composite Resins; Biomaterials Oct. 1999; 20(20); 1897–908; 1 pg.

NCBI National Library of Medicine; Crit Rev Oral Biol Med 1996; 7(2): 172–9; Bioavailability of Components of Resin–Based Materials Which are Applied to Teeth; 1 pg.

R.S. Davidson, J.W. Goodin, Eur. Polym. J. 18 (1982) pp. 597–606.

C. Dekker, Makromol. Chem. 180 (1979) pp. 2027–2030.

C.R. Morgan, A.D. Ketley, J. Radiat.Curing 7 (1980) pp. 10–13.

C.R. Morgan, F. Magnotta, A.D. Ketley, J. Polym. Sci., Polym. Ed. 15 (1977) pp. 627–645.

G. Smets, Bull. Soc. Chim. Belges 71 (1962) pp. 857–858.

G. Oster, J. Amer. Chem. Soc. 79 (1957) pp. 595–598.

P. Ferruti et al., Polymer 26 (1985) pp. 1336–1348.

H.G. Elais, Makromolekule, Huttig & Wepf, Basel 1990, p. 555.

Do Thi Bich Loan, I.m. Panayotov, Eur. Polym. J. 32 (1996) pp. 957–962.

Japanese Patent Abstract; vol. 010, No. 262 (c–371) Sep. 6, 1986.

Ferruti P. et al; "Recent Results on Functional Polymers and Macromonomers of Interestas Biomaterials or for Biomaterial Modification".

Hill I. R. C. et al; "In vitro cytotoxicity of poly (amidoamine)s: relevance to DNA delivery" BBA–General Subjects, Elsevier Science Publishers, NL, vol. 1427, No. 2; Apr. 19, 1999, pp. 161–174.

Huang, et al; "The biocompatibility evaluation of epoxy resin–based root canal sealers in vitro"; Biomaterials, Elsevier Science Publishers BV., Barking, GB; vol. 23, No. 1, Jan. 1, 2002, pp. 77–83, XP004322622.

* cited by examiner

DENTAL COMPOSITIONS COMPRISING BISACRYLAMIDES AND USE THEREOF

This application is a divisional of application Ser. No. 09/925,173, filed Aug. 9, 2001 now abandoned.

This application also claims the benefit of provisional application 60/224,670 and 60/310,572 filed on Aug. 11, 2000 and Aug. 7, 2001 respectively.

TECHNICAL BACKGROUND

Since decades the free-radical polymerization used in electrotechnics, electronics, dental industry, is combined with remarkable advantages in these fields. The frequently used acrylates and methacrylates are applied in combination with pigments and fillers or as pure polymerizable resins. It is well-known that during free-radical polymerization some side-reactions take place. One of them is the inhibition of the outer layer of the polymerizable material due to the influence of oxygen. The thickness of this layer depends on the viscosity of the polymerizable material, the degree of filling, the applied temperature and the time of polymerization. Frequently, the oxygen inhibited layer is disadvantageous due to the mechanical properties in this part are insufficient, the abrasion is higher and the toxicological/allergic potential is increased. The polymerization of very small layers is limited due to the oxygen inhibition, for example in case of covering electronic circuits by screen printing or for dental sealing materials or varnishes.

Furthermore, the conventional methacrylates that were used for dental applications are ester compound. Consequently, they hydrolysis under acidic or basic conditions that frequently leads to a long-term failure.

In order to reduce the oxygen inhibited layer different possibilities were suggested. One of them is the today well-known use of carbonyl/amine initiator systems for photochemical polymerization (R. S. Davison, J. W. Goodin, Eur.Polym.J 18 (1982) 597). Dekker used special color initiators that change triplet-oxygen into singulet-oxygen (C. Dekker, Makromol. Chem. 180 (1979) 2027). Furthermore, surface active additives were used (C. R. Morgan, A. D. Ketley, J. Radiat.Curing 7 (1980) 10) or the photochemical SH-En-Addition was applied (C. R. Morgan, F. Magnotta, A. D. Ketley, J.Polym.Sci., Polym. Ed. 15 (1977), 627).

The photochemical polymerization of monoacrylamides was studied by Smets (G. Smets, Bull.Soc.Chim.Belges 71 (1962) 857, G. Oster, J.Amer.Chem.Soc. 79 (1957) 595). A large number of bisacrylamides were described by Ferrutti (P. Ferrutti et al., Polymer 26 (1985) 1336). These bisacrylamides are solids that are soluble in water due to the secondary amide group or they comprises a piperidine group.

A combination of free-radical and Michael addition polymerization was suggest for encapsulation of electronic circuits (DD 295645; invs.: J. Klee, H.-H. Hörhold, I. Scherlitz-Hofmann).

The new synthesized bisacrylamides should be liquids in order to polymerized them without of solvents and furthermore they and the resulting polymers should be insoluble in water.

DESCRIPTION OF THE INVENTION

A dental composition that comprises at least one acrylamide selected from bisacrylamide, polyacrylamide, bis(meth)acrylamide and poly(meth)acrylamide; a polymerizable monomer; at least one amine and/or an initiator; a stabilizer; pigments and an organic and/or inorganic filler and that have an improved hydrolysis stability.

The bisacrylamide are characterized by the following formula:

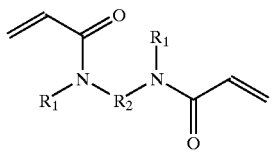

wherein $R_1$ is H or a substituted or unsubstituted $C_1$ to $C_{18}$ alkylene, substituted or unsubstituted cycloalkylene, substituted or unsubstituted $C_5$ to $C_{18}$ arylene or heteroarylene, substituted or unsubstituted $C_5$ to $C_{18}$ alkylarylene or alkylheteroarylene, substituted or unsubstituted $C_7$ to $C_{30}$ alkylene arylene, $R_2$ is a difunctional substituted or unsubstituted $C_1$ to $C_{18}$ alkylene, difunctional substituted or unsubstituted cycloalkylene, difunctional substituted or unsubstituted $C_5$ to $C_{18}$ arylene or heteroarylene, difunctional substituted or unsubstituted $C_5$ to $C_{18}$ alkylarylene or alkylheteroarylene, difunctional substituted or unsubstituted $C_7$ to $C_{30}$ alkylene arylene, Preferably bisacrylamides are characterized by the following formula:

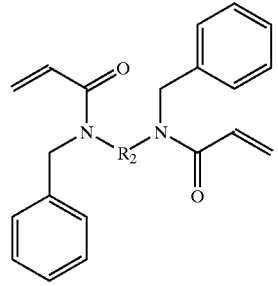

wherein $R_2$ is a difunctional substituted or unsubstituted $C_1$ to $C_{18}$ alkylene, difunctional substituted or unsubstituted cycloalkylene, difunctional substituted or unsubstituted $C_5$ to $C_{18}$ arylene or heteroarylene, difunctional substituted or unsubstituted $C_5$ to $C_{18}$ alkylarylene or alkylheteroarylene, difunctional substituted or unsubstituted $C_7$ to $C_{30}$ alkylene arylene, The claimed dental composition preferably contains as polymerizable monomer a mono- or a polyfunctional (meth)-acrylate, such as a polyalkylenoxide di- and poly-(meth)acrylate, an urethane di- and poly(meth) acrylate, a vinyl-, vinylen- or vinyliden-, acrylate- or methacrylate; preferably were used diethyleneglycol dimethacrylate, triethyleneglycol dimethacrylate, 3,(4),8,(9)-dimethacryloyloxymethyltricyclodecane, dioxolan bismethacry-late, glycerol trimethacrylate, furfuryl methacrylate or a monoacrylamide in a content of 5 to 80 wt-%.

Bisacrylamides react with amines in a thermal Michael addition polymerization. Preferably for the addition polymerization are used primary monoamines, disecondary diamines and/or polyamines of the following structure:

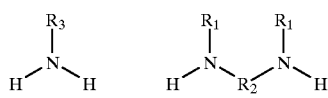 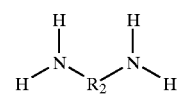 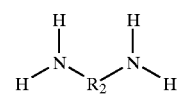

wherein

- R₁ is a substituted or unsubstituted $C_1$ to $C_{18}$ alkylene, substituted or unsubstituted cycloalkylene, substituted or unsubstituted $C_5$ to $C_{18}$ arylene or heteroarylene, substituted or unsubstituted $C_5$ to $C_{18}$ alkylarylene or alkylheteroarylene, substituted or unsubstituted $C_7$ to $C_{30}$ alkylene arylene,

- R₂ is a difunctional substituted or unsubstituted $C_1$ to $C_{18}$ alkylene, difunctional substituted or unsubstituted cycloalkylene, difunctional substituted or unsubstituted $C_5$ to $C_{18}$ arylene or heteroarylene, difunctional substituted or unsubstituted $C_5$ to $C_{18}$ alkylarylene or alkylheteroarylene, difunctional substituted or unsubstituted $C_7$ to $C_{30}$ alkylene arylene and

- R₃ is a substituted or unsubstituted $C_2$ to $C_{18}$ alkylene, substituted or unsubstituted cycloalkylene, substituted or unsubstituted $C_5$ to $C_{18}$ arylene or heteroarylene, substituted or unsubstituted $C_5$ to $C_{18}$ alkylarylene or alkylheteroarylene, substituted or unsubstituted $C_7$ to $C_{30}$ alkylene arylene, Furthermore the claimed dental composition can contain a polymerization initiator, that preferably is a thermal initiator, a redox-initiator or a photo initiator such as champhor quinone.

In order to avoid a spontaneous polymerization stabilizer are added such as a radical absorbing monomer for example hydrochinonmonomethylether, hydrochinondimethylether, 2,6-di-tert.-butyl-p-cresol.

The dental composition comprises an inorganic filler and/or an organic filler. Preferably inorganic fillers such as $La_2O_3$, $ZrO_2$, $BiPO_4$, $CaWO_4$, $BAWD_4$, $SrF_2$, $Bi_2O_3$, glasses or an organic fillers, such as polymer granulate or a combination of organic/or inorganic fillers are applied.

The dental composition is preferably usable as dental root canal filling material or as pulp capping material.

In an alternative embodiment, the bisacrylamide can have the following formula

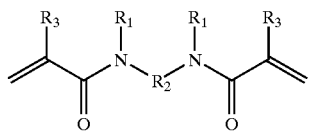

or it can be a polyacrylamide as follows

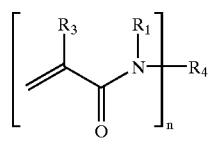

Similarly, the bis(meth)acrylamide can have the following formula

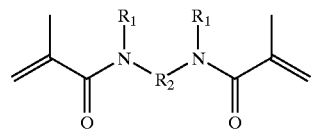

or it can be a poly (meth)acrylamide as follows

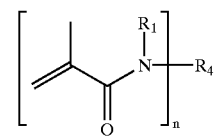

In these formulas, R1 and R3 are the same or different, and are preferably independently H or a substituted or unsubstituted C1 to C18 alkylene, substituted or unsubstituted cycloalkylene, substituted or unsubstituted C5 to C18 arylene or heteroarylene, substituted or unsubstituted C5 to C18 alkylarylene or alkylheteroarylene, substituted or unsubstituted C7 to C30 alkylene arylene; R2 is preferably a difunctional substituted or unsubstituted C1 to C18 alkylene, difunctional substituted or unsubstituted cycloalkylene, difunctional substituted or unsubstituted C5 to C18 arylene or heteroarylene, difunctional substituted or unsubstituted C5 to C18 alkylarylene or alkylheteroarylene, difunctional substituted or unsubstituted C7 to C30 alkylene arylene; and R4 is preferably a mono- or polyfunctional substituted or unsubstituted C1 to C18 alkylene, mono- or polyfunctional substituted or unsubstituted cycloalkylene, mono- or polyfunctional substituted or unsubstituted C5 to C18 arylene or heteroarylene, mono- or polyfunctional substituted or unsubstituted C5 to C18 alkylarylene or alkylheteroarylene, mono- or polyfunctional substituted or unsubstituted C7 to C30 alkylene arylene.

EXAMPLE 1

N,N'-bisacryloyl-N,N'-dibenzyl-5-oxanonanediamine-1.9: In a 4-necked 1-l-flask equipped with a stirrer, a thermometer and two 50 ml dropping funnels 102.16 g (0.3 mol) of N,N'-dibenzyl-5-oxanonanediamine-1.9 were dissolved in 300 ml of methylenechloride. After cooling to 0–5° C. 57.020 g (0.63 mol) of acryloylchloride dissolved in 30 ml of methylenechloride and 25.20 g (0.63 mol) of NaOH dissolved in 60 ml of water were added simultaneously under stirring during 1.5 hours so that the temperature remains at 0–5° C. Thereafter the mixture were stirred at room temperature for additional two hours. Than the reaction mixture were hydrolyzed with 600 ml of ice-water. The organic phase were separated and the aqueous solution were extracted twice with methylenechloride. The collected organic liquids were washed with 150 ml of 1 n HCl, 150 ml of 1 n NaHCO₃ and sometimes with 150 ml of deionised water until the water shows a pH-value of approximately 7. Than the organic solution was dried over NaSO₄. Thereafter the NaSO₄ was filtered off and to the solution 0.1346 g of 2,6-di-tert.-butyl-p-cresol were added. The methylenechloride was removed at 40° C. in vacuum and the bisacrylamide was dried.

Yield: 132.6 g (98.5% of th.), $n_D^{20}$ = 1.5499, η = 2.35 Pa*s, $M_n$ (vpo) = 450g/mol $C_{28}H_{36}N_2O_3$, 448.61    calc    C 74.97    H 8.09    N 6.24 found    C 74.50    H 8.09    N 6.24

IR: 1655 $cm^{-1}$ (CONR), 1620 $cm^{-1}$ ($CH_2$=CH—)

$^1$H-NMR: 7.4–7.2 (Ph), 6.65/4.52 ($\underline{CH_2}$Ph), 5.58/6.38 ($CH_2$=CH), 3.4–3.2 ($CH_2$O, $CH_2$N), 1.6–1.5 ($CH_2CH_2$)

$^{13}$C-NMR:  166.69/166.28 (3), 137.60/136.95 (5), 129.66/128.95 (2),
128.80/128.50 (6), 128.35/128.23 (7), 128.16/128.00 (8),
127.27/126.25 (1), 70.40/70.27 (12), 50.99/48.88 (4), 48.07/46.97 (9),
27.43/27.11 (11), 25.43/23.15 (10)

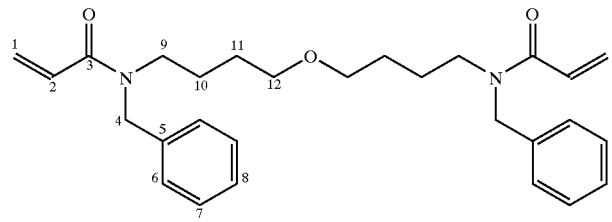

Addition Polymerization 5.000 g (11.137 mmol) of N,N'-bisacryloyl-N,N'-dibenzyl-5-oxanonanediamine-1.9 and 3.792 g (11.137 mmol) were mixed homogeneously together and reacted for 60 hours at 60° C. The addition polymer shows the following results obtained by GPC:

| $M_n$ g $mol^{-1}$ | $M_w$ g $mol^{-1}$ | $M_z$ g $mol^{-1}$ | $M_w/M_n$ | [η] ml $g^{-1}$ |
|---|---|---|---|---|
| 3615 | 9403 | 16280 | 2.60 | 8.741 |

EXAMPLE 2

N,N'-bisacryloyl-N,N'-dibenzylethylenediamine: In a 4-necked 1-l-flask equipped with a stirrer, a thermometer and two 50 ml dropping funnels 29.198 g (0.12 mol) of N,N'-dibenzylethylenediamine were dissolved in 100 ml of methylenechloride. After cooling to 0–5° C. 21.991 g (0.24 mol) of acryloylchloride dissolved in 30 ml of methylenechloride and 9.718 g (0.24 mol) of NaOH dissolved in 40 ml of water were added simultaneously under stirring during 1.5 hours so that the temperature remains at 0–5° C. Thereafter the mixture were stirred at room temperature for additional two hours. Than the reaction mixture were hydrolyzed with 600 ml of ice-water. The organic phase were separated and the aqueous solution were extracted twice with methylenechloride. The collected organic liquids were washed with 100 ml of 1 n HCl, 100 ml of 1 n $NaHCO_3$ and sometimes with 100 ml of deionised water until the water shows a pH-value of approximately 7. Than the organic solution was dried over $NaSO_4$. Thereafter the $NaSO_4$ was filtered off and to the solution 0.028 g of 2,6-di-tert.-butyl-p-cresol were added. The methylenechloride was removed at 40° C. in vacuum and the bisacrylamide was dried.

Yield: 27.9 g (65.9% of th.), $m_p$ = 75.5–76.6° C., Tg = −7.2° C., $M_n$ (vpo) = 350 g/mol $C_{22}H_{24}N_2O_2$, 348.45
calc.    C 75.83    H 6.94    N 8.04
found    C 76.00    H 7.26    N 8.05

EXAMPLE 3

N,N'-bisacryloyl-N,N'-dibenzyl-4,4'-diaminodicyclohexylamine: In a 4-necked 1-l-flask equipped with a stirrer, a thermometer and two 50 ml dropping funnels 60.551 g (0.16 mol) of N,N'-dibenzyl-4,4'-diaminodicyclohexylamine were dissolved in 150 ml of methylenechloride. After cooling to 0–5° C. 28.061 g (0.31 mol) of acryloylchloride dissolved in 30 ml of methylenechloride and 12.401 g (0.31 mol) of NaOH dissolved in 50 ml of water were added simultaneously under stirring during 1.5 hours so that the temperature remains at 0–5° C. Thereafter the mixture were stirred at room temperature for additional two hours. Than the reaction mixture were hydrolyzed with 500 ml of ice-water. The organic phase were separated and the aqueous solution were extracted twice with methylenechloride. The collected organic liquids were washed with 100 ml of 1 n HCl, 100 ml of 1 n $NaHCO_3$ and sometimes with 10 ml of deionised water until the water shows a pH-value of approximately 7. Than the organic solution was dried over $NaSO_4$. Thereafter the $NaSO_4$ was filtered off and to the solution 0.077 g of 2,6-di-tert.-butyl-p-cresol were added. The methylenechloride was removed at 40° C. in vacuum and the bisacrylamide was dried.
Yield: 54.0 g (69.9% of th.), Tg=47.1° C.

Application Example 1 (Dental Root Canal Sealer)
Bisacrylamide-Paste 5.0000 g of N,N'-bisacryloyl-N,N'-dibenzyl-5-oxanonanediamine-1.9 of example 1, 3.1642 g of Calciumtungstate, 0.7911 g of Zirconiumoxide, 0.0300 g of Aerosil and 0.0100 g of $Fe_2O_3$ were mixed homogeneously.

Amine-Paste 1.8962 g of N,N'-dibenzyl-5-oxanonanediamine-1.9, 0.8423 g of 1-Aminoadamantane, 10.9540 g of Calciumtungstate, 2.7385 g of Zirconiumoxide and 0.3353 g of Aerosil were mixed homogeneously.

Immediately before use both pastes were mixed homogeneously in a ratio of 1/1 (v/v) or 1/1.86 (w/w). The material shows an radio-opacity of 11.5 mm/mm Al.

We claim:

1. A dental composition that comprises at least a bisacrylamide, a polymerizable monomer, at least an amine and/or an initiator, a stabilizer, pigments and an organic and/or inorganic filler and that have an improved hydrolysis stability, wherein said bisacrylamide are characterized by the following formula:

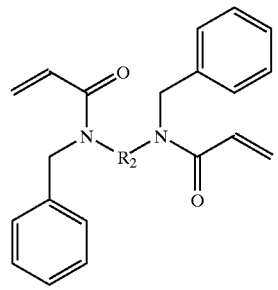

wherein
$R_2$ is a difunctional $C_1$ to $C_{18}$ alkylene, difunctional cycloalkylene, difunctional $C_5$ to $C_{18}$ arylene or heteroarylene, difunctional $C_5$ to $C_{18}$ alkylarylene or alkylheteroarylene, or difunctional $C_7$ to $C_{30}$ alkylene arylene.

* * * * *